United States Patent [19]

Haber et al.

[11] Patent Number: 5,010,590
[45] Date of Patent: Apr. 30, 1991

[54] VISOR-CAP

[76] Inventors: William Haber, 5812 Donna Ave., Tarzana, Calif. 91356; Jack Takeshita, 12816 Montague St., Pacoima, Calif. 91331

[21] Appl. No.: 360,419

[22] Filed: Jun. 2, 1989

[51] Int. Cl.$^5$ ............................................. A61F 9/00
[52] U.S. Cl. ............................................. 2/12; 2/177; 2/195; 2/209.3
[58] Field of Search .............. 2/9, 12, 15, 171, 171.1, 2/171.2, 171.3, 171.4, 171.5, 171.6, 171.7, 171.8, 172, 173, 173.5, 174, 175, 177, 192, 195, 196, 197, 200, 206, 209.1, 209.3, 209.4, 209.5, 209.7

[56] References Cited

U.S. PATENT DOCUMENTS

| | | | |
|---|---|---|---|
| 2,081,088 | 5/1937 | Guntrup | 2/12 |
| 2,447,215 | 8/1948 | Stovall | 2/174 |
| 2,827,636 | 3/1958 | Hoeflich | 2/195 |
| 2,964,757 | 12/1960 | Jarvis | 2/206 |
| 2,988,743 | 6/1961 | Wagenfeld | 2/209.3 |
| 3,266,056 | 8/1966 | DeVillers | 2/12 |
| 3,271,778 | 9/1966 | Ferguson | 2/12 |
| 4,246,659 | 1/1981 | Lyons | 2/209.3 |
| 4,335,471 | 6/1982 | Quigley | 2/12 |
| 4,670,910 | 6/1987 | Rosasco | 2/177 |
| 4,747,164 | 5/1988 | Foulke | 2/171 |
| 4,864,663 | 9/1989 | Horam | 2/200 |

FOREIGN PATENT DOCUMENTS

| | | | |
|---|---|---|---|
| 14209 | 5/1956 | Fed. Rep. of Germany | 2/177 |
| 807043 | 12/1936 | France . | |
| 836444 | 6/1960 | United Kingdom | 2/195 |
| 1018736 | 2/1966 | United Kingdom | 2/195 |
| 2168236 | 6/1986 | United Kingdom | 2/177 |

Primary Examiner—Peter Nerbun
Assistant Examiner—Diana L. Biefeld
Attorney, Agent, or Firm—Poms, Smith, Lande & Rose

[57] ABSTRACT

A visor-cap which can present a variety of display surfaces is formed from a rectangular blank of material having a unitary die-cut portion including a bill portion, a display portion, two straps whose outer ends are detachably joinable, and several structural fold lines. The rectangular blank of material has two longer and two shorter sides. The bill extends along one of the two shorter sides and the straps extend from opposite sides of the bill along the longer sides to points near the other shorter side. The display portion lies between the straps and extends to first and second points where the straps join the bill. First and second structural fold lines extend between the two points with the first line extending substantially directly between them and the second line being curved toward the bill's forward end. A third structural fold line extends across the display portion essentially parallel to the first fold line and dividing the display portion into upper and lower panels. The die-cut portion is removed from the remainder of the rectangular blank of material and is folded along the various structural fold lines to prevent various display surfaces including a single vertically extending display surface, a dual vertically extending display surface including a movable display flap, and a display surface extending substantially below the level of the bill and suitable for use as a mask in front of the visor-cap wearer's face.

8 Claims, 3 Drawing Sheets

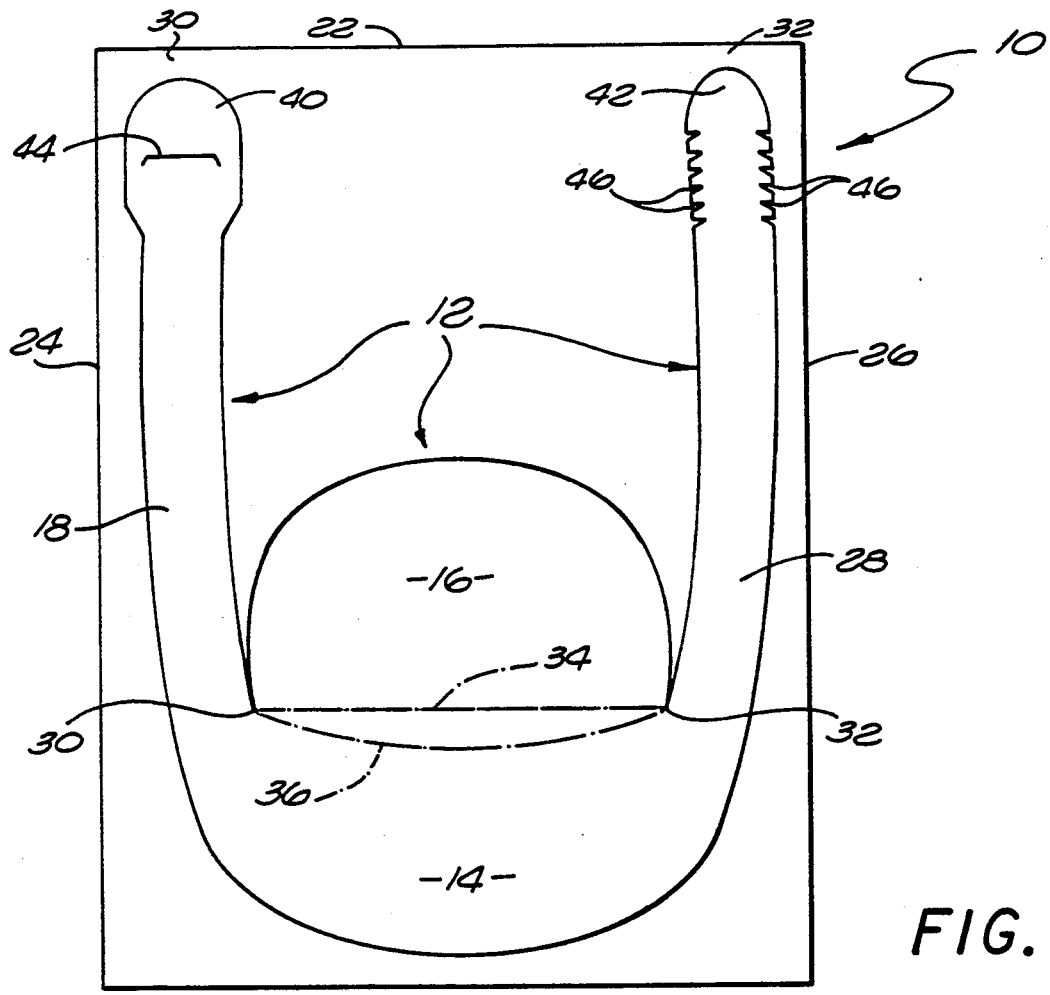
FIG. 1
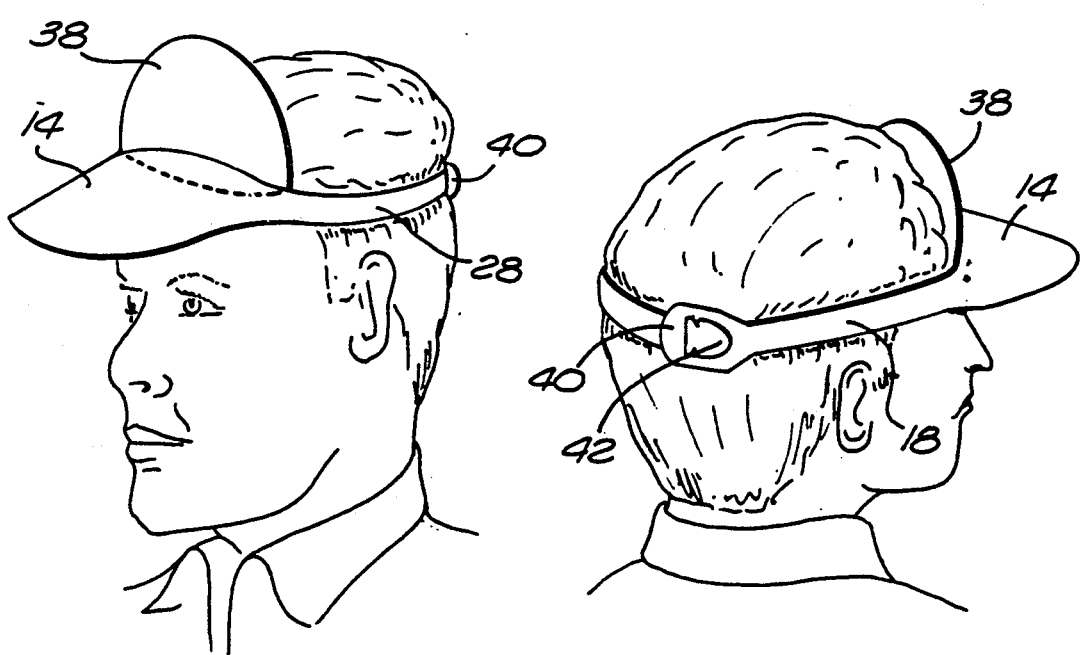
FIG. 2
FIG. 3

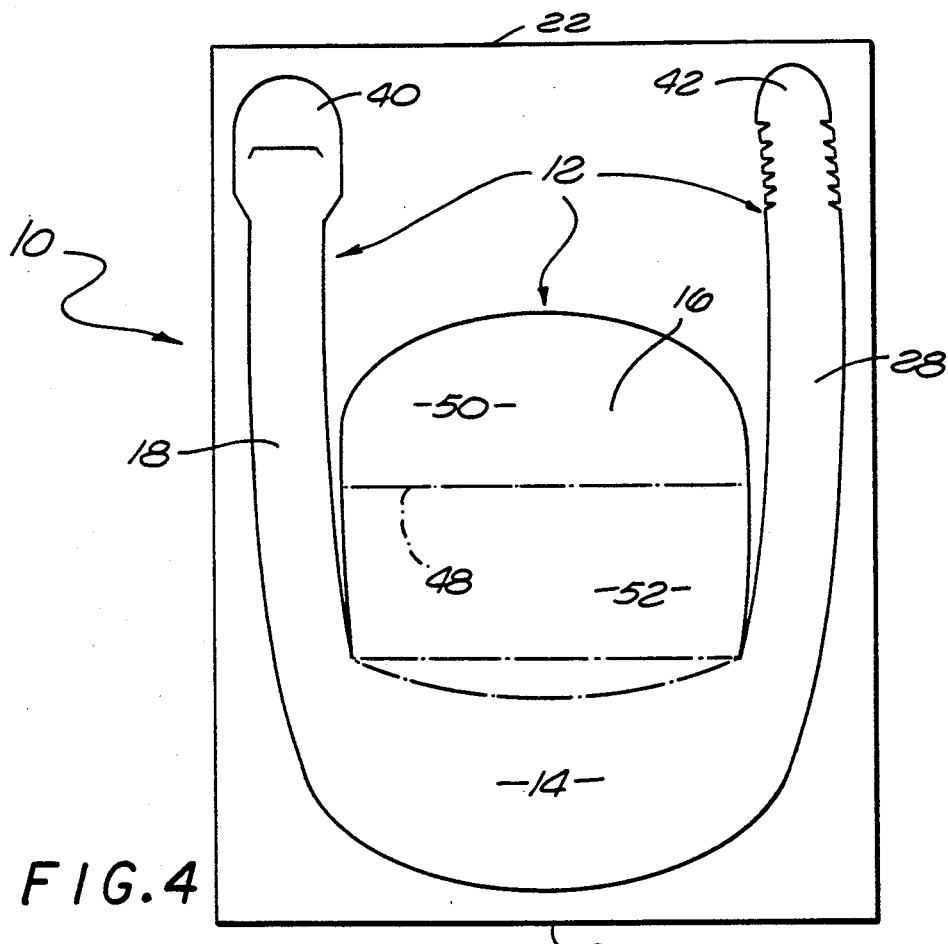
FIG. 4
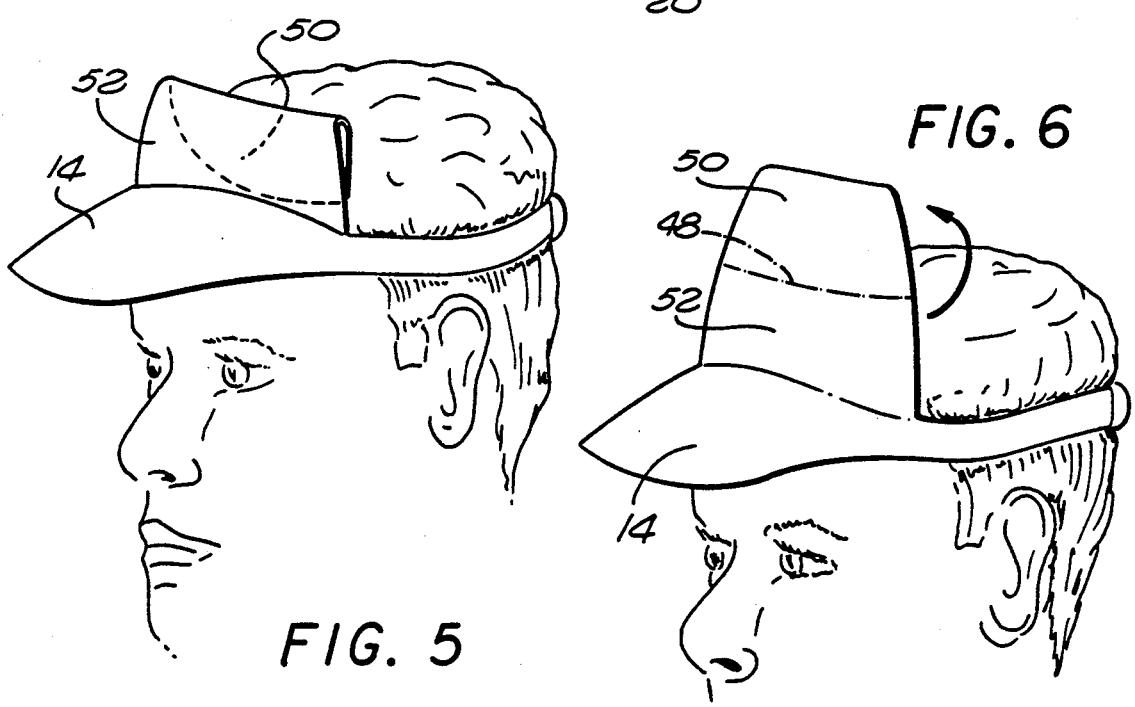
FIG. 5
FIG. 6

VISOR-CAP

FIELD OF THE INVENTION

The invention relates to visor-caps wherein the visor-cap is formed from a single sheet of die-cut material and may be folded to present various display surfaces.

BACKGROUND OF THE INVENTION

Visor-caps or caps are well-known in the art and many such caps are available on the market as novelty items, party favors, for advertising purposes and the like. Also, many such visor-caps are made from a single sheet of material. Examples of such visor-caps are shown in U.S. Pat. Nos. 4,747,164 and 4,670,910. Such aspect of such visor-caps occasionally include a display section for presenting various indicia such as slogans, logos, or other promotional material. Up to the present time, however, most such visor-caps have provided limited visibility of whatever indicia might be placed upon them.

Accordingly, it is an object of the present invention to provide a visor-cap with improved visibility of the indicia placed upon it.

Another aspect of the prior visor-caps is their inability to present more than a single display surface on a single visor-cap.

Accordingly, it is an important object of the present invention to provide a visor-cap which permits presentation of more than a single display or message on a single visor-cap by providing more than a single display surface.

A further aspect of the prior visor-caps is their inability to provide any display surface extending below their visor or bill portions.

Accordingly, it is an object of the present invention to provide a versatile visor-cap that permits its wearer to present a display surface that extends below the level of the visor.

SUMMARY OF THE INVENTION

In accordance with specific embodiments illustrating the principles of the present invention, a series of structural fold lines permit the formation, from a single sheet of die-cut material, which may be rectangular, for example, of a versatile visor-cap which can present a variety of display surfaces.

In a preferred embodiment, a visor-cap is formed from a single sheet of rectangular material and includes a unitary die-cut portion having a brim or bill portion, a crown or display portion and two straps The sheet of rectangular material has two longer and two shorter sides and may be formed of heavyweight paper, lightweight cardboard or other suitable material that may be flexed and folded.

The bill portion extends generally along one of the two shorter sides and the two straps extend from opposite sides of the bill along the two longer sides to points adjacent the other shorter side. The crown or display portion lies between the two straps and extends to first and second points where the straps join the bill. First and second structural fold lines also extend between these two points with the first fold line extending substantially directly between them and the second fold line being curved toward the forward end of the bill.

In this embodiment, the die-cut portion is removed or separated from the rest of the rectangular material and formed into a visor-cap by first folding the bill down along the curved fold line, then folding the display portion up along the straight fold line, and finally flexing the opposite sides of the bill rearward to lock the folded sections into place. The resulting visor-cap has a downwardly sloping bill and a relatively rigid vertically extending display area that is clearly visible to anyone looking at the visor-cap wearer.

The visor-cap or hat is made ready for wearing by joining together the outer ends of the two straps. The outer end of one strap has a slot cut into it and the outer end of the other strap has edges formed into a series of slanted notches. The notched end may be inserted into the slotted end to form a band that can encircle a wearer's head. The slanting of the notches makes it slightly easier to insert than to remove the notched end from the slot, thereby providing a positive locking action between the outer ends of the two straps. The visor-cap may be adjusted to a large range of head sizes simply by drawing the notched end through the slot an appropriate distance.

Another aspect of the invention involves an optional third structural fold line extending across the display portion and essentially parallel to the first fold line thereby dividing the display portion into upper and lower panels. When the die-cut portion has been removed from the rectangular sheet of material and made ready for wearing as a visor-cap by performing the previously described folds and strap end joining, the third fold line may be utilized to present a dual display configuration. The upper display area panel may be folded along the third fold line downward and behind the lower display area panel, thereby leaving only the lower panel visible to those looking at the visor-cap wearer. A single display or message may be placed on this panel. Then, at the visor-cap wearer's discretion, the folded down upper panel may be flipped up either to present a second display or message, or to add something to the display or message on the lower panel thereby changing that display or message.

A further embodiment of the present invention involves optionally extending the upper end of the display or crown portion towards the side of the rectangular material opposite the side where the bill portion extends. This creates a generally larger display area that is particularly well suited to the dual display configuration previously discussed.

Concerning yet another embodiment of the present invention, the display portion of the die-cut portion may be extended to be adjacent the side of the rectangular material opposite the side where the bill portion extends. The third structural fold line is positioned so as to divide the display portion into a large upper panel and a small lower panel. After generally forming the visor-cap by using the first two fold lines and joining the straps, the upper panel may be folded along the third fold line down and behind the lower panel to present a lower display area that extends below the level of the visor or bill and in front of the wearer's face. This configuration is suitable for displaying a mask in front of the wearer's face while simultaneously having an upper display area, in the form of the lower panel of the original display portion, that can present either a message, a logo, or some type of continuation of the lower display area's mask, such as hair or a balding head.

A further aspect of the mask embodiment of the invention involves the use of only the second fold line, which extends between the points where the straps join the bill and which curves toward the forward end of the bill. In this configuration, after the die-cut portion is removed from the rest of the rectangular material, the entire extended display portion may be folded down along the second fold line to present a single display area extending below the level of the visor and in front of the wearer's face. This configuration permits the die-cut portion's entire display portion to be used to present a mask and results in no part of the display portion extending above the visor.

An advantage of the present invention is that the die-cut rectangular sheets of heavy paper or light cardboard may be initially used as placemats or the like at a luncheon or dinner, and later may be formed into caps with advertising or a message relating to the sponsor of the event.

Other objects, features and advantages will become apparent from a consideration of the following detailed description and from the accompanying drawings.

BRIEF DESCRIPTION OF THE DRAWINGS

FIG. 1 is a top plan view of a rectangular blank of material showing the die-cut portion used to form a visor-cap or hat;

FIG. 2 is a perspective view of the front of a formed visor-cap;

FIG. 3 is a perspective view of the rear of a formed visor-cap;

FIG. 4 is a top plan view of a rectangular blank of material showing the die-cut portion used to form a dual display embodiment of a visor-cap;

FIG. 5 is a front perspective view of an alternative embodiment visor-cap showing a dual display surface with one surface on display;

FIG. 6 is a front perspective view of an alternative embodiment visor-cap showing a dual display surface with both surfaces on display;

DETAILED DESCRIPTION

Figure 7:
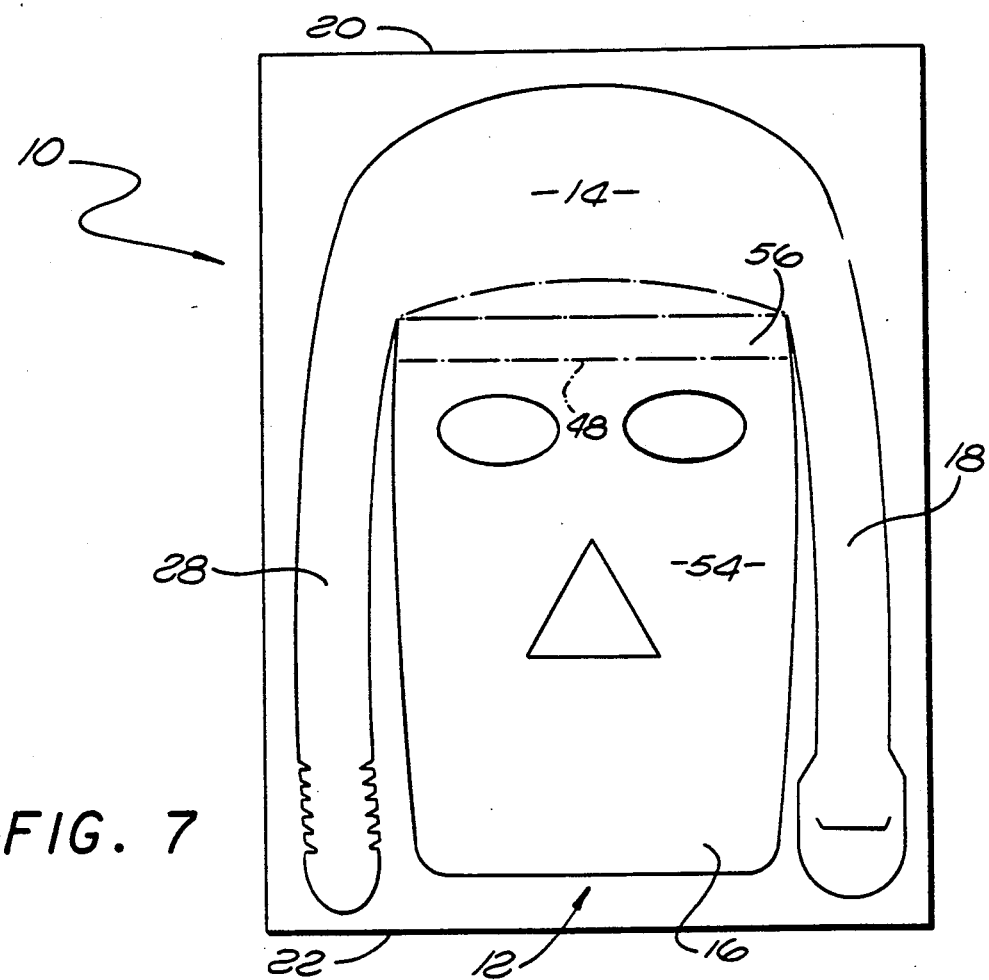
FIG. 7 is a top plan view of a rectangular blank of material showing the die-cut portion used to form a dual display embodiment of a visor-cap.

Referring more particularly to the drawings, FIG. 1 is a top plan view of a rectangular blank of material 10 with a die-cut portion 12 illustrating the principles of the present visor-cap or hat invention. The die-cut portion 12 of the visor-cap of FIG. 1 includes a brim or bill portion 14, a crown or display portion 16, and two straps 18, 28. The rectangular blank of material 10 is provided with two shorter sides 20, 22 and two longer sides 24, 26. It may be noted that the rectangular blank of material 10 may be formed of lightweight cardboard, heavy paper, or any other suitable material capable of being folded and flexed.

In accordance with one embodiment of the invention, as illustrated in FIG. 1, the bill portion 14 extends generally along one of the shorter sides 20 and the two straps 18, 28 extend from opposite sides of the bill 14 along the longer sides 24, 26 to points along the other shorter side 22. The display portion 16 lies between the two straps 18, 28 and extends to first and second points 30, 32 adjacent where the straps 18, 28 join the bill 14.

A first structural fold line 34 extends substantially directly between the first and second points 30, 32, and a second structural fold line 36 also extends between the first and second points 30, 32 and is curved toward the forward end of the bill 14 and the nearer of the shorter sides 20.

In practice, the die-cut portion 12 is separated from the rest of the rectangular blank of material 10 and formed into a visor-cap by folding the bill 14 down along the second structural fold line 36, folding the display portion 16 up along the first structural fold line 34, and flexing the opposite sides of the bill 14 rearward. As is most clearly illustrated in FIG. 2, the flexing of the sides of the bill 14 locks the folded sections into place and provides a visor hat or cap with a curved, downwardly sloping bill and a relatively rigid, vertically extending display area 38. It may be noted that the vertical disposition of the display area 38 of this embodiment of the present invention provides improved viewing regarding any indicia, logo, or other matter placed on the display area 38.

Small bridging elements may extend across the die-cuts every inch or at similar regular spacings, so that the rectangular sheet 10 maintains its integrity and may be employed as a placemat or the like prior to its use as a visor hat or cap.

Formation of the visor-cap is completed by joining together the outer ends 40, 42 of the straps 18, 28. The outer end of one strap 40 has a slot 44 cut into it and the outer end of the other strap 42 has edges formed into a series of slanted notches 46. As is best seen in FIG. 3, the notched end 46 may be inserted into the slot 44 to form a band that can encircle a wearer's head. It may be noted that the slanting of the notches makes it easier to insert than to remove the notched end 46 from the slot, thereby providing a positive locking action between the outer ends 40, 42 of the straps 18, 28. It may also be noted that the above described notch/slot arrangement allows for adjustment of the visor-cap to a large range of head sizes simply by drawing the notched end 42 through the slot 44 an appropriate distance.

FIG. 4 illustrates a further aspect of the present invention. A third structural fold line 48 extends across the display portion 16 essentially parallel to the first fold line 34 thereby dividing the display area 38 into substantially equal upper 50 and lower 52 panels. After removing the die-cut portion 12 from the rectangular blank of material 10 and generally forming the visor-cap or hat by performing the previously described folds and strap end joining, the third fold line 48 may be used to provide a dual display configuration. As is best illustrated in FIGS. 5 and 6, the upper display area panel 50 may be folded down and behind the lower display area panel 52, thereby leaving only the lower panel 52, and any display or message present on that panel, visible to those looking at the visor-cap wearer. Then, at the visor-cap wearer's discretion, the folded down upper panel 50 may be flipped up. It may be noted that the third structural fold line 48, and its accompanying movable upper display area panel 50, provide a unique dual display configuration which allows either the presentation of a second distinct and separate display or message on the movable upper panel 50, or the presentation on the upper panel 50 of a display or message which adds to or modifies the display or message on the lower display area panel 52.

As is illustrated in FIG. 4 the display portion 16 may be extended towards the short side 22 of the rectangular blank of material opposite the short side 20 where the bill 14 extends. This results in a larger display area 38 that is well suited to the previously discussed dual display configuration.

FIG. 7 illustrates a further embodiment of the present invention. The display portion 16 is extended to be adjacent the short side 22 of the rectangular blank of material 10 opposite the short side 20 along which extends the bill 14. The third structural fold line 48 is positioned so as to divide the display area 38 into a large upper display area panel 54 and a small lower display area panel 56. After generally forming the visor-cap by using the first two fold lines 34, 36 and joining the strap ends 40, 42, the large upper panel 54 is folded along the third fold line 48 down and behind the small lower panel 56. The large panel 54 then presents a display area extending below the level of the bill 14 and in front of a wearer's face. The small display panel 56 extends vertically above the bill 14. It may be noted that this configuration provides a dual display format suitable for displaying a mask in front of the visor-cap wearer's face while simultaneously having a small display panel 56 extending above the bill on which may be presented a message or logo, or some type of continuation of the mask display such as hair, a balding head or the like.

Figures 8, 9:
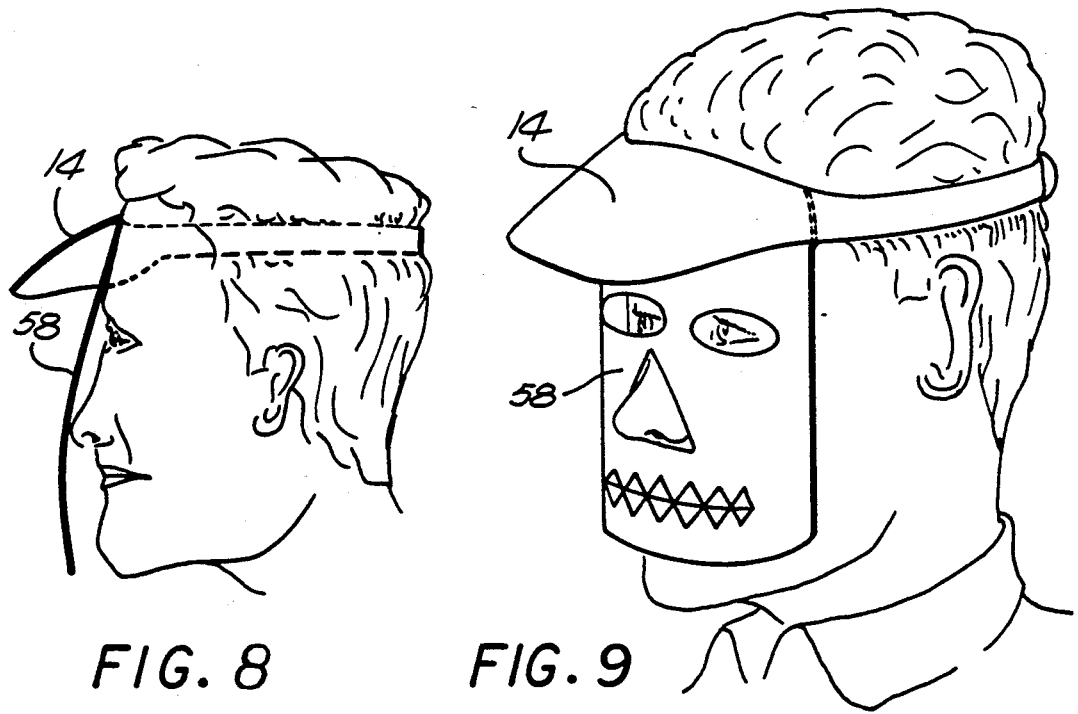
FIG. 8 is a side view of an alternative embodiment visor-cap showing a display surface extending below the visor.
FIG. 9 is a front perspective view of an alternative embodiment visor-cap showing a display surface extending below the visor.

As is best illustrated in FIGS. 8 and 9, a further aspect of the above described mask embodiment involves forming a visor-cap using only the second structural fold line 36. In this configuration, after the die-cut portion 12 is removed from the blank of rectangular material 10, the entire extended display portion 16 is folded along the second fold line 36 down and behind the bill 14 thereby presenting a single large display area 58 extending below the level of the bill 14 and in front of the wearer's face. It may be noted that this configuration allows for a relatively full-face mask to extend in front of a wearer's face and results in no part of the display portion 16 extending above the bill 14.

In conclusion, it is to be understood that the foregoing description and accompanying drawings relate to only one preferred embodiment of the present invention. Other embodiments may be utilized without departing from the spirit and scope of the invention. Thus, by way of example and not of limitation, the invention could be made of materials other than those discussed herein. Also, the third structural fold line 48 may be positioned at any one of numerous places on the display portion 12 to vary the size and extent of the previously described dual display configuration. It may be noted that the third structural fold line 48 serves to distinguish the present invention from other visor-caps in the prior art. See for example French Patent No. 807,043 which includes no such structural fold, and uses separate retaining straps. Also, by way of example and not of limitation, the means for joining the outer ends 40, 42 of the straps 18, 28 may be other than the slot 44 and notch 46 approach discussed herein. Accordingly, it is to be further understood that the detailed description and drawings set forth hereinabove are for illustrative purposes only and do not constitute a limitation on the scope of the invention.

What is claimed is:

1. A fully rectangular sheet of a single type of die-cut material suitable for use as a place mat, for forming a visor-cap comprising:
   a fully rectangular blank of a single type of material having two longer sides and two shorter sides;
   a unitary die-cut portion of said rectangular blank having a bill extending generally along one of said shorter sides, two straps affixed to opposite sides of said bill and extending generally along said longer sides to points adjacent the other shorter side and including mating joining means, and a crown portion formed between said straps and extending to first and second points at opposite sides of said bill; and
   first and second structural fold lines extending between said first and second points, the first of said fold lines extending substantially directly between said two points, and the second of said fold lines being curved toward the forward end of said bill;
   whereby said sheet may be initially used as a place mat or the like, and then said die-cut portion may be separated from said rectangular blank, and said crown and said bill may be formed into a visor-cap by folding at said two fold lines and securing said straps together by said joining means.

2. A sheet for forming a visor-cap as defined in claim 1 wherein said die-cut material comprises lightweight cardboard.

3. A sheet for forming a visor-cap as defined in claim 1 wherein a portion of said crown portion may be upwardly folded along said first fold line to form a vertically extending surface including display means on said surface for exposure during visor-cap wearing.

4. A sheet for forming a visor-cap as defined in claim 1 wherein said crown portion is divided into upper and lower panels by a third structural fold line essentially parallel to said first structural fold line and said crown portion may be upwardly folded along said first fold line to form a vertically extending display surface including display means on said surface for exposure during visor-cap wearing, and said crown portion may be further folded along said dividing fold line to form a flap from said upper panel that may be raised or lowered to add to or take away from said display surface.

5. A sheet for forming a visor-cap as defined in claim 1 wherein said crown portion extends substantially to said other shorter side and said crown portion may be downwardly folded along said first fold line to form a surface extending generally in front of a wearer's face and including display means on said surface for exposure during visor-cap wearing.

6. A sheet for forming a visor-cap as defined in claim 1 wherein said crown portion extends substantially to said other shorter side and is divided into upper and lower panels by a third structural fold line essentially parallel to said first structural fold line and said lower panel may be upwardly folded along said first fold line to form a vertically extending upper display surface including display means on said upper display surface for exposure during visor-cap wearing, and said upper panel may be folded along said third fold line down and behind said lower panel to form a lower display surface extending generally in front of a wearer's face and including display means on said lower display surface for exposure during visor-cap wearing.

7. A fully rectangular sheet of a single type of die-cut material suitable for use as a place mat, for forming a visor-cap comprising:
   a fully rectangular blank of a single type of material having two longer sides and two shorter sides;
   a unitary die-cut portion of said rectangular blank having a bill extending generally along one of said shorter sides, two straps affixed to opposite sides of said bill and extending generally along said longer sides to points adjacent the other shorter side and including mating joining means, and a crown portion formed between said straps and extending to first and second points at opposite sides of said bill;

said mating joining means including one of said straps having an outer end with a slot formed therein, and the other of said straps having edges formed into notches constituting means for insertion and locking into said slot;

first and second structural fold lines extending between said first and second points, the first of said fold lines extending substantially directly between said two points, and the second of said fold lines being curved toward the forward end of said bill; and said crown portion being divided into upper and lower panels by a third structural fold line essentially parallel to said first structural fold line and said crown portion may be upwardly folded along said first fold line to form a vertically extending display surface including display means on said surface for exposure during visor-cap wearing, and said crown portion may be further folded along said dividing fold line to form a flap from said upper panel that may be raised or lowered to add to or take away from said display surface;

whereby said sheet may be initially used as a place mat or the like, and then said die-cut portion may be separated from said rectangular blank, and said crown and said bill may be formed into a visor-cap by folding at said two fold lines and securing said straps together by said joining means.

8. A fully rectangular sheet of a single type of die-cut material suitable for use as a placement, for forming a visor-cap comprising:

a rectangular blank of material having two longer sides and two shorter sides;

a unitary die-cut portion of said rectangular blank having a bill extending generally along one of said shorter sides, two straps affixed to opposite sides of said bill and extending generally along said longer sides to points adjacent the other shorter side and including mating joining means, and a crown portion formed between said straps and extending to first and second points at opposite sides of said bill;

first and second structural fold lines extending between said first and second points, the first of said fold lines extending substantially directly between said two points, and the second of said fold lines being curved toward the forward end of said bill;

said crown portion extending substantially to said other shorter side of said blank and being divided into upper and lower panels by a third structural fold line essentially parallel to said first structural fold line and said lower panel may be upwardly folded along said first fold line to form a vertically extending upper display surface including display means on said upper display surface for exposure during visor-cap wearing, and said upper panel may be folded along said third fold line down and behind said lower panel to form a lower display surface extending generally in front of a wearer's face and including display means on said lower display surface for exposure during visor-cap wearing; and die-cut areas in said lower display panel located to form viewing openings for a user's eyes, whereby said die-cut portion may be separated from said rectangular blank, and said crown and said bill may be formed into a visor-cap by folding at said two fold lines and securing said straps together by said joining means.

* * * * *